(12) United States Patent
Tada

(10) Patent No.: US 12,123,831 B2
(45) Date of Patent: *Oct. 22, 2024

(54) MEASUREMENT CHIP, MEASURING DEVICE AND MEASURING METHOD

(71) Applicant: Furuno Electric Co., Ltd., Hyogo (JP)

(72) Inventor: Keiji Tada, Nishinomiya (JP)

(73) Assignee: FURUNO ELECTRIC CO., LTD., Nishinomiya (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/991,851

(22) Filed: Nov. 22, 2022

(65) Prior Publication Data

US 2023/0097717 A1 Mar. 30, 2023

Related U.S. Application Data

(60) Division of application No. 16/801,159, filed on Feb. 26, 2020, now Pat. No. 11,543,347, which is a
(Continued)

(30) Foreign Application Priority Data

Aug. 31, 2017 (JP) ................................ 2017-167388

(51) Int. Cl.
G01N 21/41 (2006.01)
G01N 21/27 (2006.01)
G01N 21/77 (2006.01)

(52) U.S. Cl.
CPC ........... G01N 21/41 (2013.01); G01N 21/272 (2013.01); G01N 21/77 (2013.01);
(Continued)

(58) Field of Classification Search
CPC ...... G01N 21/41; G01N 21/272; G01N 21/77; G01N 21/7703; G01N 2021/418; G01N 2021/7776; G01N 33/543
See application file for complete search history.

(56) References Cited

U.S. PATENT DOCUMENTS 5,030,420 A 7/1991 Bacon et al.
5,866,430 A 2/1999 Grow
(Continued)

FOREIGN PATENT DOCUMENTS

EP 0884581 A1 12/1998
EP 1483547 A1 12/2004
(Continued)

OTHER PUBLICATIONS

"Surface plasmon resonance," Wikipedia, Retrieved from the Internet URL: https://en.wikipedia.org/wiki/Surface_plasmon_resonance, on Feb. 21, 2020, 19 pages.
(Continued)

*Primary Examiner* — Samuel P Siefke
*Assistant Examiner* — Henry H Nguyen
(74) *Attorney, Agent, or Firm* — XSENSUS LLP

(57) ABSTRACT

The present disclosure is to provide a measurement chip, a measuring device, and a measuring method which can accurately estimate an analyte concentration with a simple configuration. A measurement chip may include a propagation layer, an introductory part, a drawn-out part and a reaction part. Through the propagation layer, light may propagate. The introductory part may introduce the light into the propagation layer. The drawn-out part may draw the light from the propagation layer. The reaction part may have, in a surface of the propagation layer where a reactant that reacts to a substance to be detected is formed, an area where a content of the reactant changes monotonously in a perpendicular direction perpendicular to a propagating direction of the light, over a given length in the propagating direction.

16 Claims, 14 Drawing Sheets

Related U.S. Application Data continuation-in-part of application No. PCT/JP2018/029512, filed on Aug. 7, 2018.

(52) U.S. Cl.
CPC ... *G01N 21/7703* (2013.01); *G01N 2021/418* (2013.01); *G01N 2021/7776* (2013.01)

(56) References Cited

U.S. PATENT DOCUMENTS

| | | | |
|---|---|---|---|
| 6,469,785 | B1 | 10/2002 | Duveneck et al. |
| 10,732,104 | B2 | 8/2020 | Tada et al. |
| 2002/0074513 | A1 | 6/2002 | Abel et al. |
| 2004/0038386 | A1 | 2/2004 | Zesch et al. |
| 2004/0257579 | A1* | 12/2004 | Shirai .............. G01N 21/45 356/477 |
| 2005/0070027 | A1 | 3/2005 | Gollier et al. |
| 2005/0162659 | A1* | 7/2005 | Freeman .............. G01N 21/45 356/477 |
| 2005/0239210 | A1 | 10/2005 | Iida |
| 2007/0146718 | A1 | 6/2007 | Takase et al. |
| 2010/0103429 | A1 | 4/2010 | Cottier |
| 2014/0350221 | A1 | 11/2014 | Schasfoort et al. |
| 2015/0204723 | A1 | 7/2015 | Zheng et al. |
| 2018/0202930 | A1 | 7/2018 | Tada et al. |

FOREIGN PATENT DOCUMENTS

| | | |
|---|---|---|
| JP | 2013-061179 A | 4/2013 |
| WO | 2017/006679 A1 | 1/2017 |

OTHER PUBLICATIONS

Fan, X., et al., "Sensitive optical biosensors for unlabeled targets: A review," Analytica Chimica Acta, vol. 620, © 2008 Elsevier B.V. All rights reserved, Published online May 18, 2008, pp. 8-26.

Extended European search report issued on Apr. 13, 2021, in corresponding European patent Application No. 18850542.4, 8 pages.

Chen Zhou et al., "Multifunctional waveguide interferometer sensor: simultaneous detection of refraction and absorption with size-exclusion function", Optics Express, vol. 26, No. 19, Sep. 17, 2018, pp. 24372-24383.

Fang et al., "Resonant Waveguide Grating Bio-sensor for Living Cell Sensing", 2006, Biophysical Journal, 1925-1940 (Year: 2006).

Office Action mailed Sep. 5, 2024, in European Patent Application No. 18850542.4, 6 pages.

Paul D. Coffey et al, "Multiple path length dual polariztion interferometry", Optics Express, vol.17, No. 13, Jun. 16, 2009, pp. 10959-10969, XP093199623, total 11 pages.

\* cited by examiner

——— ONLY LIGAND EXISTS
······· NO LIGAND AND ANALYTE EXISTS

——— LIGAND AND ANALYTE EXIST
······· NO LIGAND AND ANALYTE EXISTS

— AMPLITUDE
······ PHASE WHEN LIGAND AND ANALYTE EXIST
— — PHASE WHEN NO LIGAND AND ANALYTE EXISTS

— AMPLITUDE
······ PHASE WHEN LIGAND AND ANALYTE EXIST
— — PHASE WHEN NO LIGAND AND ANALYTE EXISTS

······ NO LIGAND AND ANALYTE EXISTS
— — ONLY LIGAND EXISTS
—— LIGAND AND ANALYTE EXIST

······ NO LIGAND AND ANALYTE EXISTS
— — ONLY LIGAND EXISTS
—— LIGAND AND ANALYTE EXIST

MEASUREMENT CHIP, MEASURING DEVICE AND MEASURING METHOD

CROSS-REFERENCE TO RELATED APPLICATIONS

This application is a Divisional of U.S. application Ser. No. 16/801,159, filed Feb. 26, 2020, which is a bypass continuation-in-part of PCT International Application No. PCT/JP2018/029512, filed on Aug. 7, 2018, which claims priority to Japanese Patent Application No. 2017-167388, filed on Aug. 31, 2017, the entire disclosure of each is incorporated herein by reference.

TECHNICAL FIELD

The present disclosure relates to a measurement chip, a measuring device, and a measuring method.

BACKGROUND

Conventionally, some techniques for detecting a substance to be detected (hereinafter, referred to as "analyte") are proposed. For example, Nonpatent Document 1 discloses surface plasmon resonance. Moreover, Nonpatent Document 2 discloses Mach-Zehnder. Nonpatent Document 3 discloses a technique for detecting antibody immobilized beads which couple to a film surface of an optical waveguide through antigen which is analyte.

Patent Document 1 discloses a measurement chip in which a reactant (hereinafter, referred to as "ligand") which reacts to analyte is formed in stripe manner on an upper surface of a propagation layer. The technique of Patent Document 1 utilizes a difference in amounts of phase change between an area in which the ligand is fixed and an area where the ligand is not fixed, so that the existence or the concentration of the analyte is estimated based on a change in the pattern of light.

REFERENCE DOCUMENT OF CONVENTIONAL ART

Patent Document

Patent Document 1: WO2017/006679A1
Nonpatent Document 1: Surface plasmon resonance, [online], [Searched on Aug. 2, 2017], Internet <URL: ja.wikipedia.org/wiki.
Nonpatent Document 2: Xudong Fan, Ian M. White, Siyka I. Shopova, Hongying Zhu, Jonathan D. Suter, Yuze Sun,
"Sensitive optical biosensors for unlabeled targets," analytica chimica acta, Aug. 26, 2008, P. 7
Nonpatent Document 3: Ichiro Tono, "Simple Fixed-amount Inspection Technology for Small Clinical Examination Equipment Using Optical Waveguide," TOSHIBA REVIEW, 2012, Vol. 67 No. 5, p. 61

However, the surface plasmon resonance disclosed in Nonpatent Document 1 has on a principle a problem that the sensitivity becomes low. Therefore, an expensive measuring device is needed for the surface plasmon resonance.

Moreover, the Mach-Zehnder disclosed in Nonpatent Document 2 is high in the sensitivity, but since a three-dimensional waveguide is needed, it also becomes expensive.

The technique disclosed in Nonpatent Document 3 has a problem that a secondary antibody (antibody immobilized beads) is needed when detecting an antigen as the analyte.

Moreover, the technique of Patent Document 1 is difficult to calculate an absolute phase difference because a phase difference of the intensity ratio between the 0th-order diffraction light and the 1st-order diffraction light becomes almost 0° when the phase difference reaches 360°. Patent Document 1 does not recognize the problem when the phase difference exceeds 360°. Similarly, other conventional art documents do not recognize the problem when the phase difference exceeds 360° in the measurement technique based on the phase change.

One purpose of the present disclosure is to provide a measurement chip, a measuring device, and a measuring method, capable of accurately estimating an analyte concentration with a simple configuration.

SUMMARY

A measurement chip may include a propagation layer, an introductory part, a drawn-out part and a reaction part. Through the propagation layer, light may propagate. The introductory part may introduce the light into the propagation layer. The drawn-out part may draw the light from the propagation layer. The reaction part may have, in a surface of the propagation layer where a reactant that reacts to a substance to be detected is formed, an area where a content of the reactant changes monotonously in a perpendicular direction perpendicular to a propagating direction of the light, over a given length in the propagating direction.

According to the present disclosure, an analyte concentration can be accurately estimated with a simple configuration.

DETAILED DESCRIPTION

Figure 1:
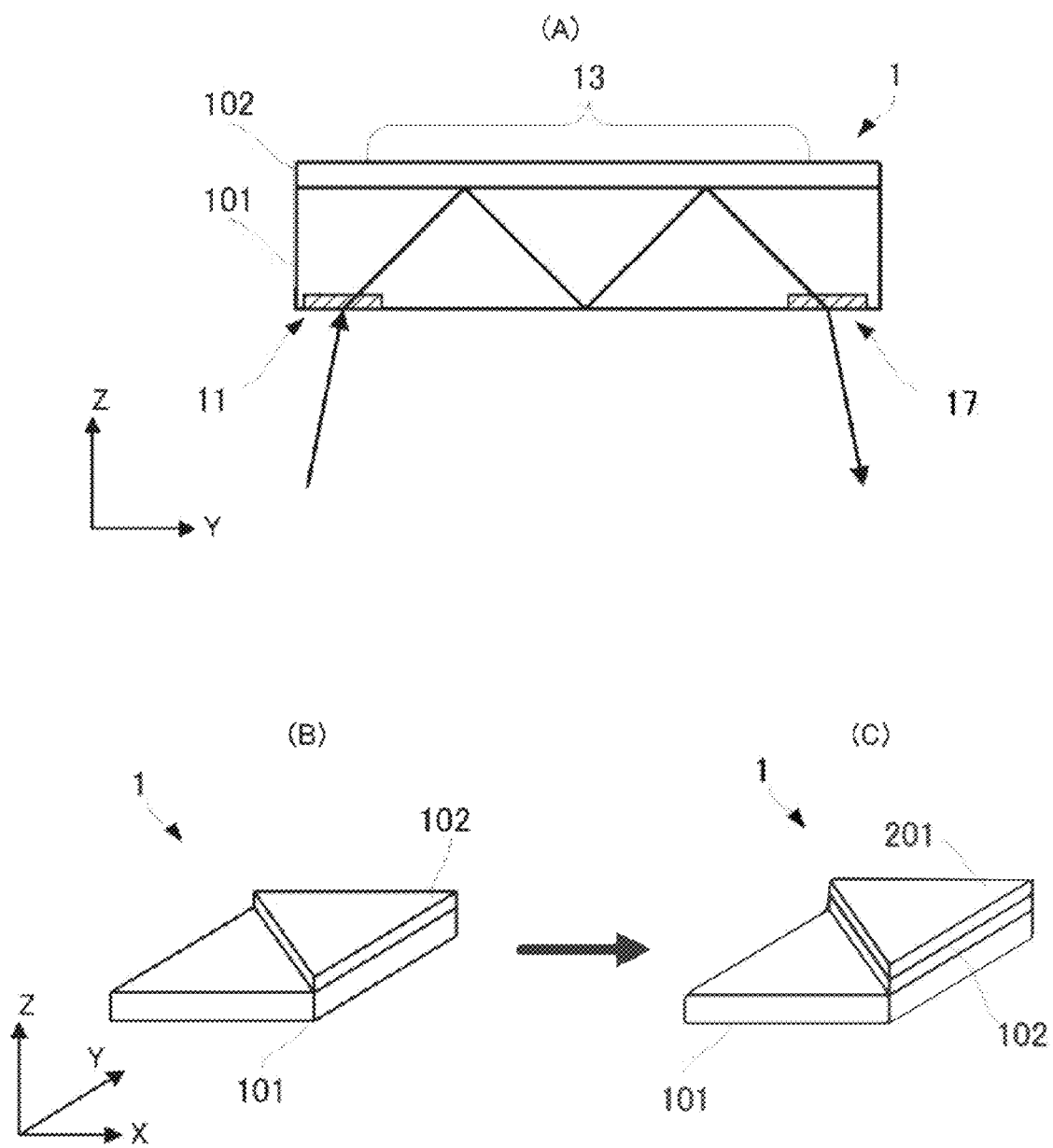
FIG. 1(A) is a cross-sectional view of a chip 1.
FIGS. 1(B) and 1(C) are perspective views of the chip 1.
Figure 2:
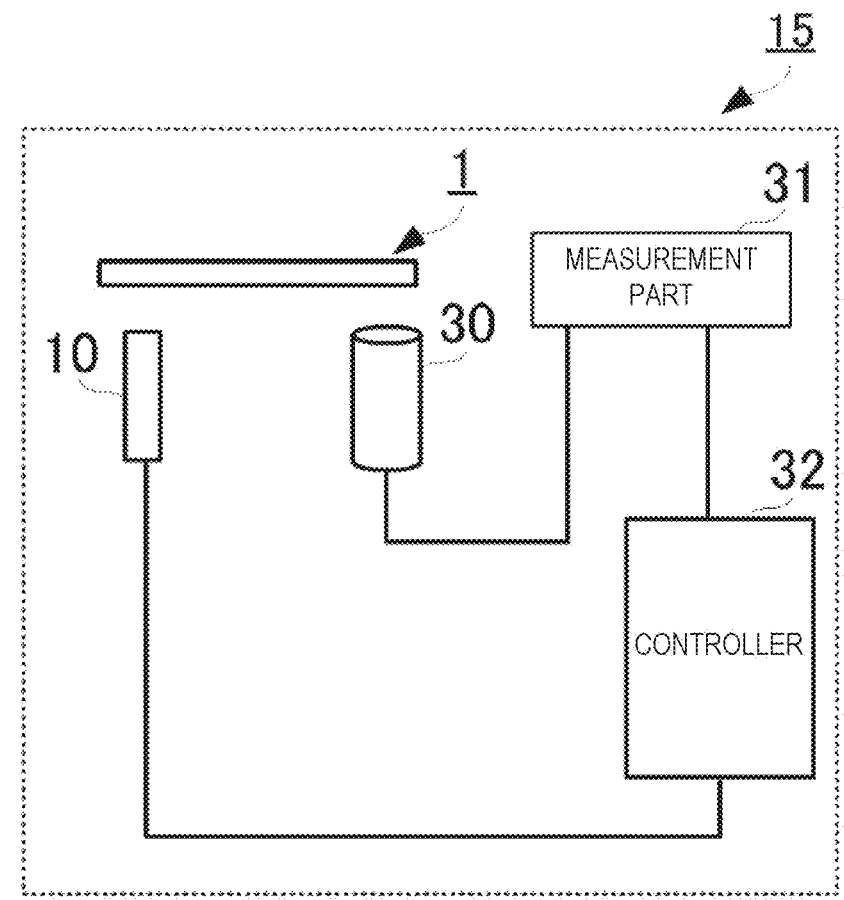
FIG. 2 is a view illustrating an outline configuration of a measuring device 15.
Figure 3:
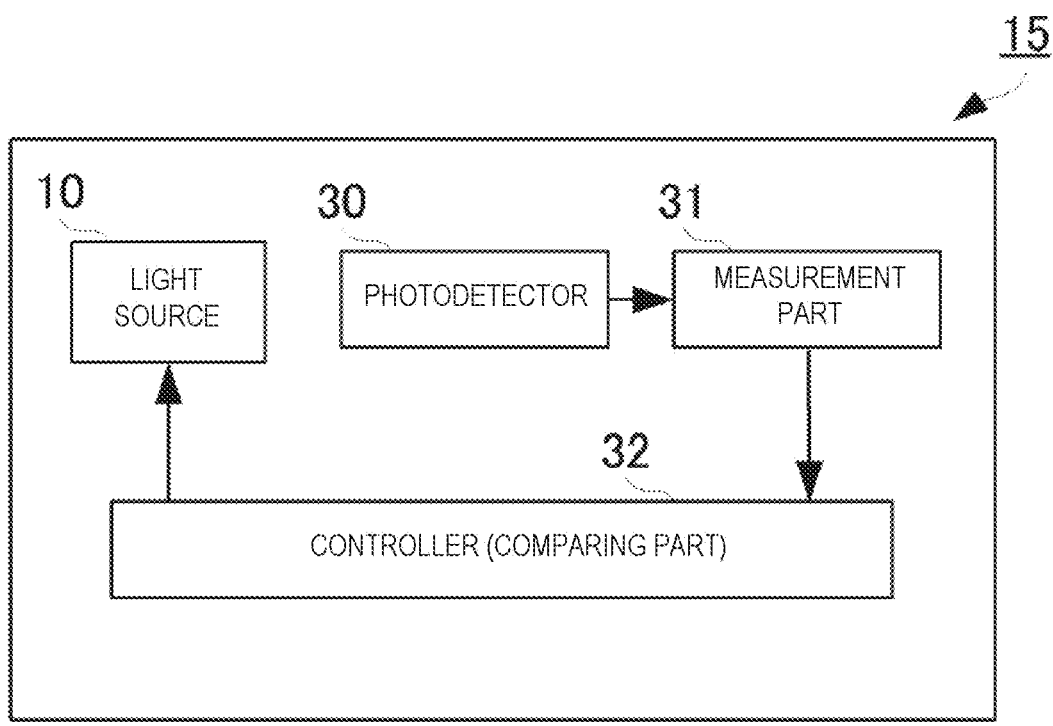
FIG. 3 is a block diagram illustrating a configuration of the measuring device 15.

FIG. 1 is a view illustrating a structure of a chip 1 which is one example of a measurement chip of the present disclosure. FIG. 2 is a view illustrating an outline configuration of a measuring device 15 including the measurement chip. FIG. 3 is a block diagram illustrating a configuration of the measuring device 15.

As illustrated in FIGS. 2 and 3, the measuring device 15 may include the measurement chip 1 (hereinafter, referred to as "the chip"), a light source 10, a photodetector 30, a measurement part 31, and a controller (comparing part) 32. Although the measurement part 31 and the controller 32 may be hardware for exclusive use, they may be implemented by software mounted on information processing equipment, such as a personal computer.

The light source 10 may be a light source which emits visible light, for example, of about 650 nm. The light may be irradiated to an introductory part 11 of the chip 1. The light emitted from the light source 10 may be desirably a gauss beam. Since the gauss beam does not change in the general form of the pattern of the light (amplitude distribution) during the process of propagation, it may be suitable for detecting a change in the pattern of light (amplitude distribution). Moreover, the light emitted from the light source 10 may be desirably a continuous wave (CW wave). By using the continuous wave, observation may become easier, and the cost of the light source can be reduced. Note that this gauss beam does not need to be in a two-dimensionally Gaussian distribution and may be a Gaussian distribution in X-direction illustrated in FIG. 1. Moreover, the light emitted from the light source 10 may not be limited to visible light, but, if particularly using the visible light, since neither a relatively expensive light source nor a relatively expensive measurement part is used for infrared light, ultraviolet light, etc., the cost of the measuring device can be reduced.

FIG. 1(A) is a cross-sectional view of the chip 1, and FIGS. 1(B) and 1(C) are perspective views of the chip 1. In this example, an upper surface direction of the chip 1 (the thickness direction) is set as "Z," a propagating direction of light is set as "Y" and a perpendicular direction perpendicular to the propagating direction of light is set as "X." Note that, unless otherwise particularly described, suppose the surface indicates one of the upper surface and the lower surface, and both surfaces indicate both the upper surface and the lower surface.

The chip 1 may be comprised of a flat-plate-like propagation layer 101. Acrylic resin of which an index of refraction is about 1.5 may be used for the propagation layer 101. However, the propagation layer 101 may use dielectrics, such as glass, polyvinyl alcohol, polyvinyl chloride, silicone resin, or polystyrene, other than the acrylic resin.

As one example, the length of the propagation layer 101 in the Z-direction is 0.1 mm, the length in the Y-direction is about 15 mm, and the length in the X-direction is 2 mm.

The introductory part 11 and a drawn-out part 17 may be provided to the lower surface of the propagation layer 101. The introductory part 11 and the drawn-out part 17 are comprised of, for example, a diffraction grating. The diffraction grating is created, for example, by a nano imprint technique. The nano imprint technique is a technique in which molds made of metal etc. where a stripe-like structure is patterned is prepared, and the pattern is transferred to the propagation layer 101. The introductory part 11 and the drawn-out part 17 may be provided by using a prism, other than the technique.

The light introduced into the introductory part 11 may be totally reflected on the upper surface and the lower surface of the propagation layer 101. This area of the propagation layer 101 which carries out the total reflection may be referred to as "the propagation part 13." The light propagated through the propagation part 13 may be drawn from the drawn-out part 17.

As illustrated in FIG. 1(B), ligand 102 may be formed in the upper surface of the propagation layer 101 (fixed in a specific pattern). As illustrated in FIG. 1(C), the ligand 102 may be a substance (reactant) which reacts (couples) specifically with analyte 201 which is a substance to be detected in an object to be measured (e.g., sample). The propagation layer 101 may include an area of the upper surface where the content of the ligand 102 changes monotonously in the perpendicular direction perpendicular to the propagating direction of the light, covering a given length in the propagating direction of the light. The content of the ligand 102 can be obtained by multiplying the content density of the ligand 102 per unit length in the propagating direction of the light by the given length.

In this example, the area where the ligand 102 is fixed may vary in the length in the propagating direction of the light (Y-direction) along the perpendicular direction (X-direction) perpendicular to the propagating direction of the light. In FIG. 1(B), as one example, the area where the ligand 102 is fixed is a right angled triangular shape in a plan view, and the length in the Y-direction is continuously and linearly lengthened in the X-direction.

Formation of the ligand 102 may be carried out by obliquely masking the upper surface of the propagation layer 101, for example, with a rubber sheet, and fixing the ligand 102 by using a surface preparation agent for fixing the ligand 102. As one example, the thickness of the fixed ligand 102 is about 5 nm.

Thus, the upper surface of the propagation layer 101 where the ligand 102 is formed may function as a reaction part which changes the phase distribution of propagating light in the X-direction due to a change in the index of refraction in the circumference of the propagation layer 101

(in this embodiment, the upper surface of the propagation layer 101) caused by a reaction (coupling) of the analyte 201 and the ligand 102.

Figure 4A:
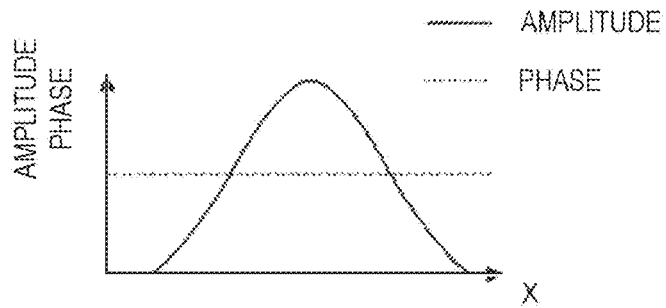
FIG. 4(A) is a view illustrating a distribution of amplitude and a phase of light introduced into an introductory part 11 in this embodiment.

FIG. 4(A) is a view illustrating a distribution of amplitude and a phase of light introduced into the introductory part 11. In this example, the light introduced into the introductory part 11 may be the gauss beam, its phase in the X-direction may be almost equal, and therefore, the general form of the pattern (amplitude distribution) of the light may not change during a propagation process.

The light introduced into the introductory part 11 may propagate inside the propagation part 13 of the propagation layer 101 while being totally reflected. Here, the index of refraction of the ligand 102 (e.g., about 1.5) may differ from the index of refraction of a surrounding part (e.g., the sample of 1.33 in the index of refraction or the air of 1 in the index of refraction). An amount of phase shift during the total reflection may depend on the index of refraction of the surrounding part which contacts the propagation part 13. Therefore, the amount of phase shift during the total reflection may differ between the area where the ligand 102 is fixed and the area where the ligand 102 is not fixed.

Figure 4B:
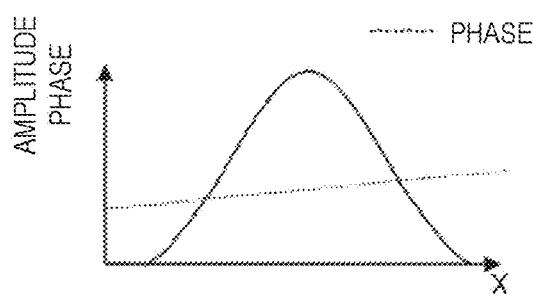
FIGS. 4(B) and 4(C) are views illustrating a distribution of amplitude and a phase of the light drawn from a drawn-out part 17 in this embodiment.

Therefore, the light propagating in the propagation part 13 may change in the phase distribution in the X-direction. As described above, the length in the Y-direction of the area where the ligand 102 is fixed may continuously and linearly be lengthened in the X-direction. Therefore, as illustrated in FIG. 4(B), the phase distribution of the light drawn from the drawn-out part 17 may incline in the X-direction. That is, the moving direction of light may vary.

Figure 4C:
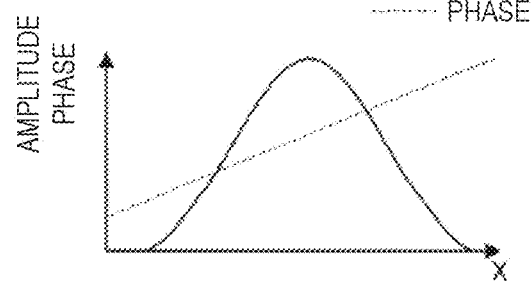
Figure 4D:
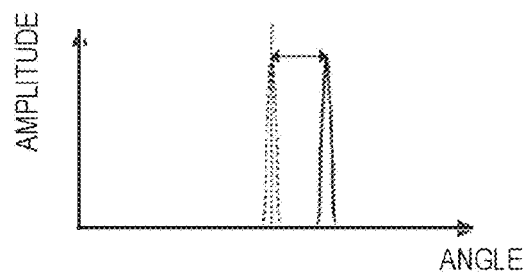
FIGS. 4(D) and 4(E) are views illustrating an amplitude distribution of light in a far-field in this embodiment.
Figure 4E:
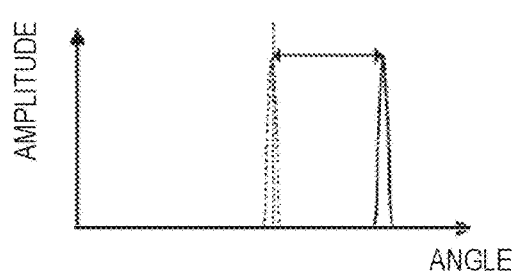
Figure 5:
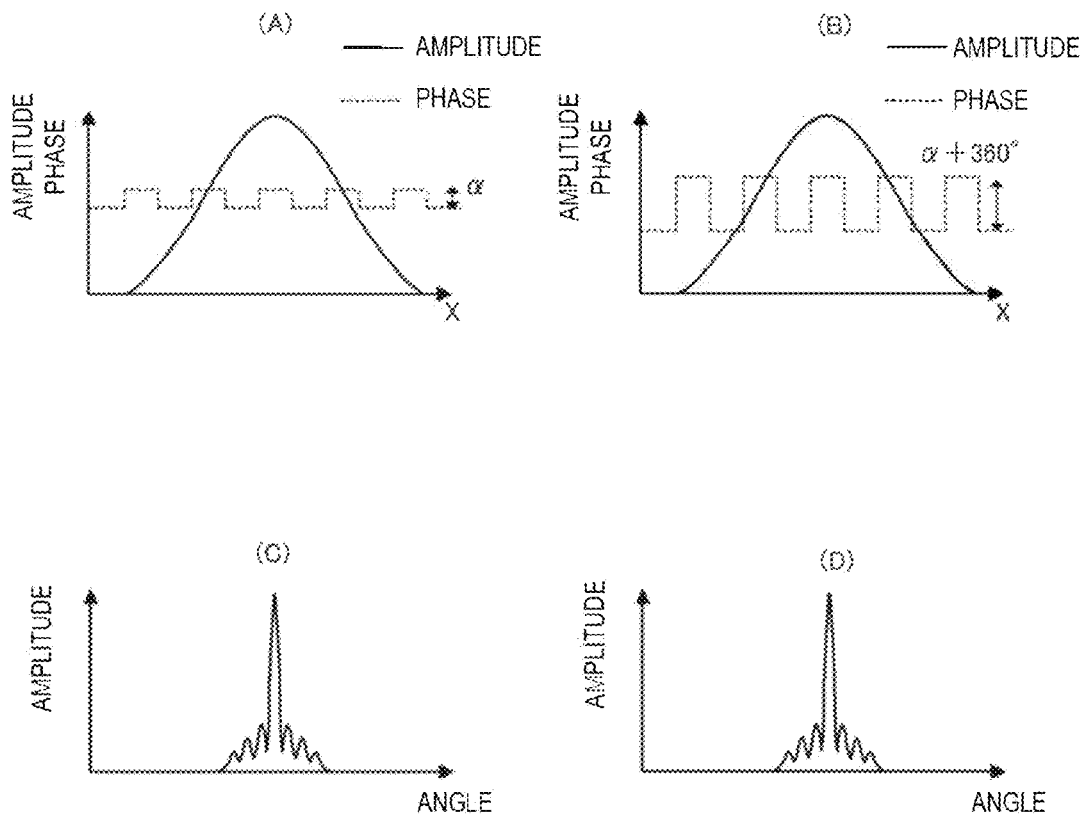
FIGS. 5(A) and 5(B) are views illustrating a distribution of amplitude and a phase of the light drawn from a drawn-out part in a reference example.
FIGS. 5(C) and 5(D) are views illustrating an amplitude distribution of light in the far-field in a reference example.

Here, as illustrated in FIG. 1(C), when the analyte 201 having the index of refraction about the same as that of the ligand 102 is coupled to the ligand 102, the amount of phase shift during the total reflection changes compared with the amount of phase shift before coupling of the analyte 201. As a result, as illustrated in FIG. 4(C), the phase distribution of the light drawn from the drawn-out part 17 may become larger in the slope in the X-direction. That is, the moving direction of the drawn light may change depending on the existence of the analyte 201.

Therefore, the measuring device 15 may receive, in a far-field (or through a Fourier transform lens) by the photodetector 30, the light drawn from the drawn-out part 17 before and after the chip 1 contacts the sample, and measure a change in a peak angle by the measurement part 31. The change in the peak angle measured by the measurement part 31 may be inputted into the controller 32, and may be recorded on a memory (not illustrated). The controller 32 may estimate that the analyte 201 exists, when the change in the peak angle is a given value or above. Alternatively, the controller 32 may estimate the concentration of the analyte 201 based on an amount of change in the peak angle. Thus, the controller 32 may perform an analysis in which the change in the pattern of light is analyzed. Moreover, the controller 32 may perform an analysis in which a change in the moving direction of light is analyzed.

Thus, the measuring device 15 may function as a measuring device which estimates the existence or the concentration of the analyte 201 (e.g., antigens, such as an influenza virus).

Referring to FIGS. 5 to 8, a difference in the technical idea between the measurement chip of this embodiment and the measurement chip disclosed in WO2017/006679A1 (reference example) is described. FIGS. 5(A) and 5(B) are views illustrating a distribution of the amplitude and the phase of the light drawn from the drawn-out part 17 in the reference example, and FIGS. 5(C) and 5(D) are views illustrating an amplitude distribution of the light in the far-field in the reference example. FIGS. 6(A) and 6(B) are views illustrating a distribution of the amplitude and the phase of the light drawn from the drawn-out part 17 in this embodiment, and FIGS. 6(C) and 6(D) are views illustrating an amplitude distribution of the light in the far-field in this embodiment.

As illustrated in FIGS. 5(A) and 5(B), in the reference example, when the phase difference on the X-axis of the light drawn from the drawn-out part 17 between the portion where the ligand 102 is fixed and the portion where the ligand 102 is not fixed reaches 360° ($\alpha+360°$), since an intensity ratio of 0th-order diffraction light and 1st-order diffraction light becomes the same state as the case where the phase difference is 0° ($\alpha+0°\approx\alpha+360°$) as illustrated in FIGS. 5(C) and 5(D), it may be difficult to estimate the absolute amount of phase difference.

Figure 6A:
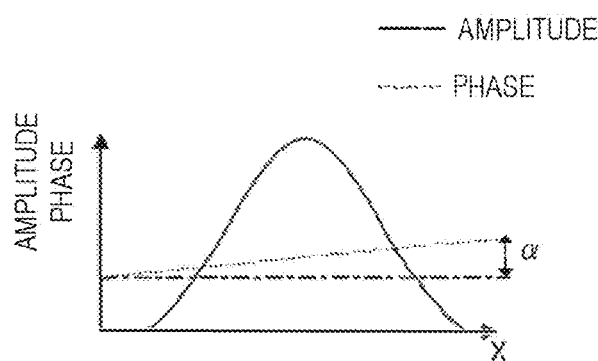
FIGS. 6(A) and 6(B) are views illustrating a distribution of amplitude and a phase of the light drawn from the drawn-out part 17 in this embodiment.
Figure 6B:
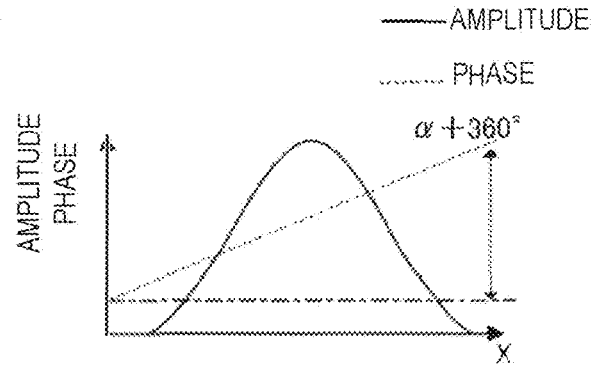
Figure 6C:
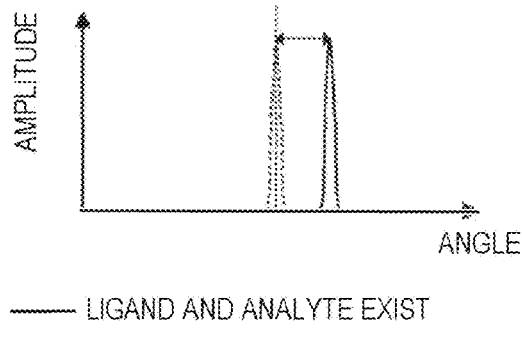
FIGS. 6(C) and 6(D) are views illustrating an amplitude distribution of light in the far-field in this embodiment.
Figure 6D:
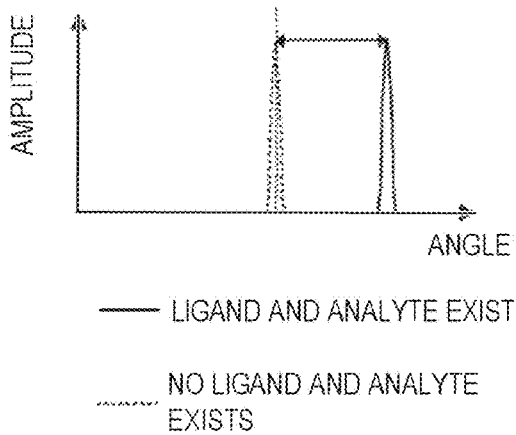
Figure 7:
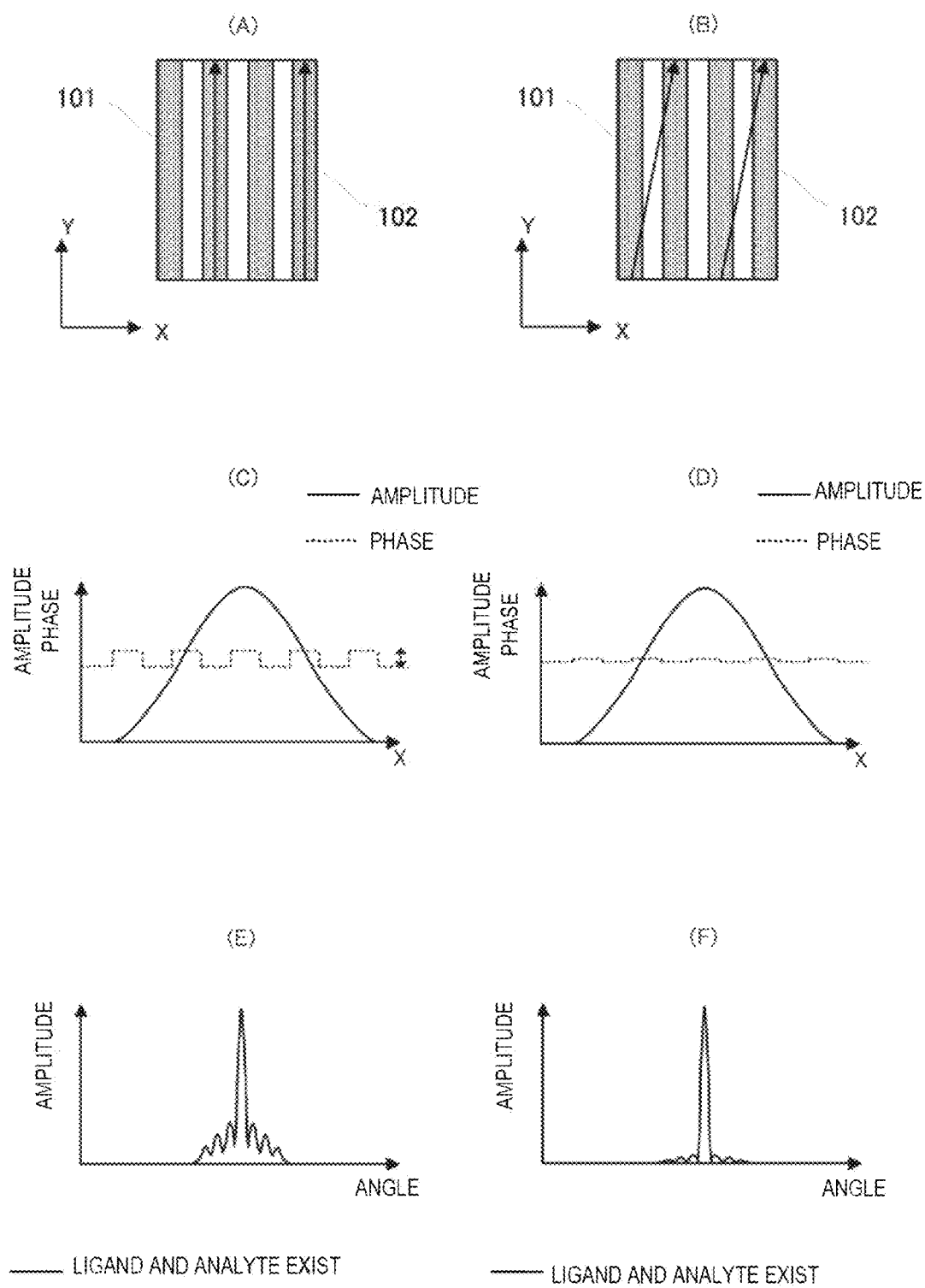
FIGS. 7(A) and 7(B) are plan views illustrating a propagating direction of light in a propagation part 13 in the reference example.
FIGS. 7(C) and 7(D) are views illustrating a distribution of amplitude and a phase of the light drawn from a drawn-out part 17 in the reference example.
FIGS. 7(E) and 7(F) are views illustrating an amplitude distribution of light in the far-field in the reference example.

On the other hand, in the measurement chip of this embodiment, the moving direction of light may change almost linearly according to the slope of the phase. That is, as illustrated in FIGS. 6(A) and 6(B), even when the phase difference of the light drawn from the drawn-out part 17, between both ends on the X-axis reaches 360°, the moving direction of light may continue changing with the slope of the phase. Therefore, as illustrated in FIGS. 6(C) and 6(D), even when the phase difference of the light drawn from the drawn-out part 17, between both ends on the X-axis exceeds 360°, the peak angle of light observed in the far-field may change according to the slope of the phase.

Thus, an amount of fixation of the ligand 102 can be estimated by measuring the amount of change in the peak angle (the difference of the peak angle between the state where the ligand 102 is fixed and the state where the ligand 102 is not fixed) only by the ligand 102, before the sample contacts (or after the sample contacts, when the coupling has hardly taken place). Here, the peak angle in the state where the ligand 102 is not fixed can be obtained by referring to light which propagates another path (e.g., light which propagates through a base material, if a measurement chip comprised of the base material and the propagation layer which are separately provided).

As described above, the technique disclosed in this embodiment can estimate the amount of fixation of the ligand 102. Therefore, the controller 32 can estimate the coupling ratio of the analyte 201 to the ligand 102 based on the amount of change in the peak angle. For example, if the ligand 102 is used as an antibody and the analyte 201 is used as an antigen, supposing the molecular weight of the antibody is about 150 kDa and the molecular weight of the antigen is 16 kDa, 21.3% ($16 \times 2/150$) of the change in the peak angle occurs theoretically when there is coupling of 2 molecules of the antigen per 1 molecule of all the antibodies (maximum coupling). Therefore, the controller 32 can estimate the coupling ratio of the antigen based on the amount of change in the peak angle, and can estimate the antigen concentration with high precision, regardless of the variation in the fixed amount of antibodies.

Figure 8A:
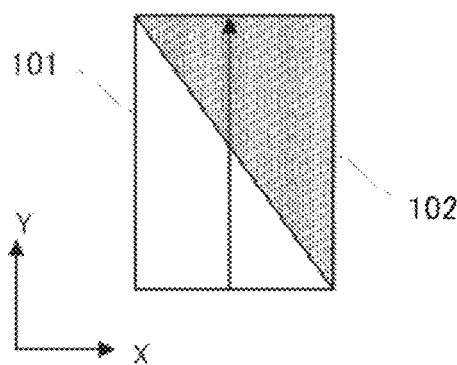
FIGS. 8(A) and 8(B) are plan views illustrating a propagating direction of light in a propagation part 13 in this embodiment.
Figure 8B:
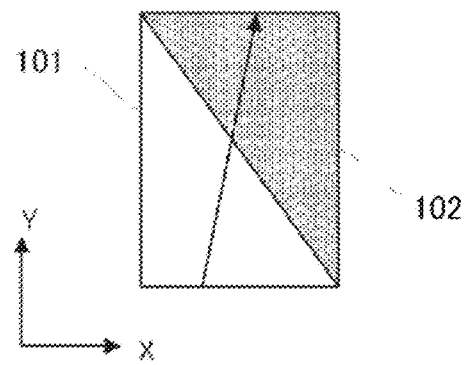

Next, FIGS. 7(A) and 7(B) are plan views illustrating a propagating direction of the light in a propagation part 13 in the reference example, FIGS. 7(C) and 7(D) are views illustrating a distribution of the amplitude and the phase of the light drawn from a drawn-out part 17 in the reference example, and FIGS. 7(E) and 7(F) are views illustrating an amplitude distribution of the light in the far-field in the reference example. FIGS. 8(A) and 8(B) are plan views illustrating a propagating direction of the light in the propagation part 13 in this embodiment, FIGS. 8(C) and 8(D) are views illustrating a distribution of the amplitude and the phase of the light drawn from the drawn-out part 17 in this embodiment, and FIGS. 8(E) and 8(F) are views illustrating an amplitude distribution of the light in the far-field in this embodiment.

As illustrated in FIGS. 7(A) and 7(B), in the reference example, if the propagating direction of the light inclines, and the lengths of the light which propagates the area where the ligand 102 is fixed and the area where the ligand 102 is not fixed become the same, the phase distribution of the light drawn from the drawn-out part 17 becomes close to a straight line, as illustrated in FIGS. 7(C) and 7(D). Therefore, in the reference example, the intensity of the 1st-order diffraction light may become remarkably low.

Figure 8C:
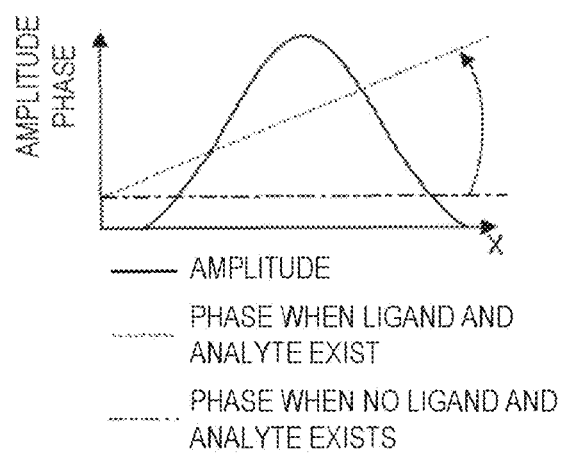
FIGS. 8(C) and 8(D) are views illustrating a distribution of amplitude and a phase of the light drawn from the drawn-out part 17 in this embodiment.
Figure 8D:
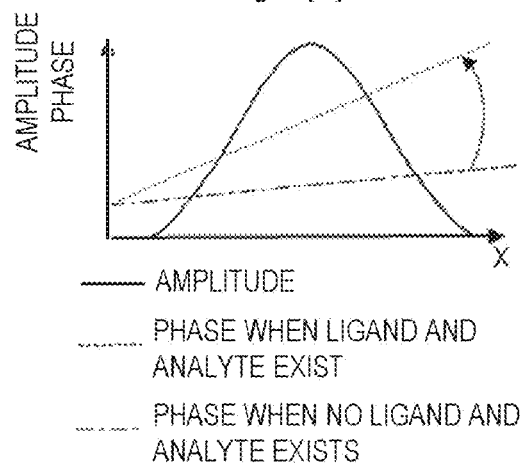
Figure 8E:
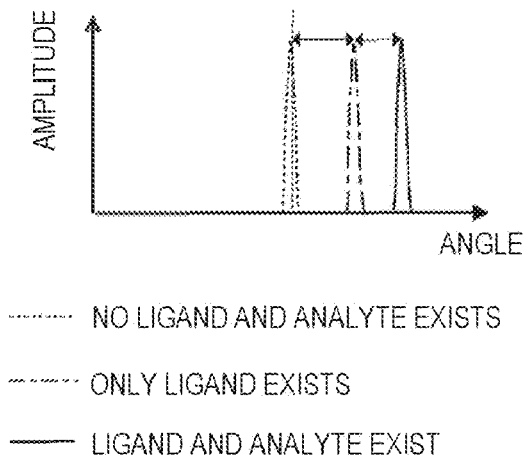
FIGS. 8(E) and 8(F) are views illustrating an amplitude distribution of light in the far-field in this embodiment.
Figure 8F:
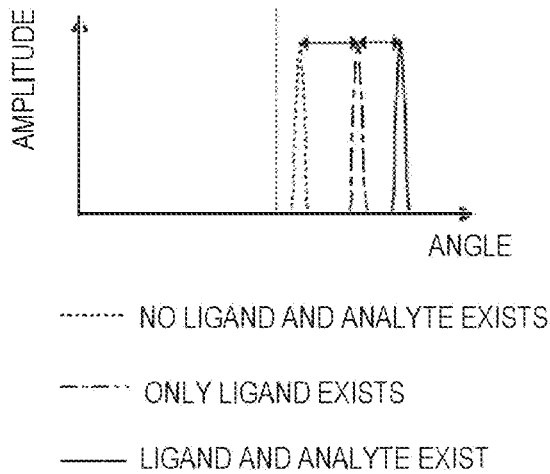

On the other hand, in this embodiment, when the propagating direction of the light inclines as illustrated in FIGS. 8(A) and 8(B), the total amount of change in the slope of the phase on the X-axis of the light drawn from the drawn-out part 17 (a difference of the slope between a case there are the ligand 102 and the analyte 201 and a case where there are not) may present a little difference, but the difference is not as remarkable as the reference example, as illustrated in FIGS. 8(C) and 8(D). Moreover, as illustrated in FIGS. 8(E) and 8(F), even if the propagating direction of the light inclines, a ratio of the amount of change in the peak angle by the analyte 201 (a difference of the peak angle between a case there are the ligand 102 and the analyte 201, and a case where there is only the ligand 102), and the amount of change in the peak angle only by the ligand 102 (a difference of the peak angle between the case there is only the ligand 102, and a case where there is no ligand 102 and analyte 201) may hardly present a difference.

On the other hand, the coupling ratio of the analyte 201 to the fixed ligand 102 can be estimated based on the ratio of the amount of change in the peak angle by the analyte 201 to the amount of change in the peak angle only by the ligand 102. Therefore, as described above, even if the propagating direction of the light inclines, since the ratio hardly differs, the technique of this embodiment can stably (robustly) estimate the concentration of the analyte 201, regardless of the variation of the light in the propagation part 13 in the propagating direction.

Therefore, the present disclosure can more accurately estimate the concentration of the analyte 201 with a simpler configuration than the conventional technique.

Figure 9:
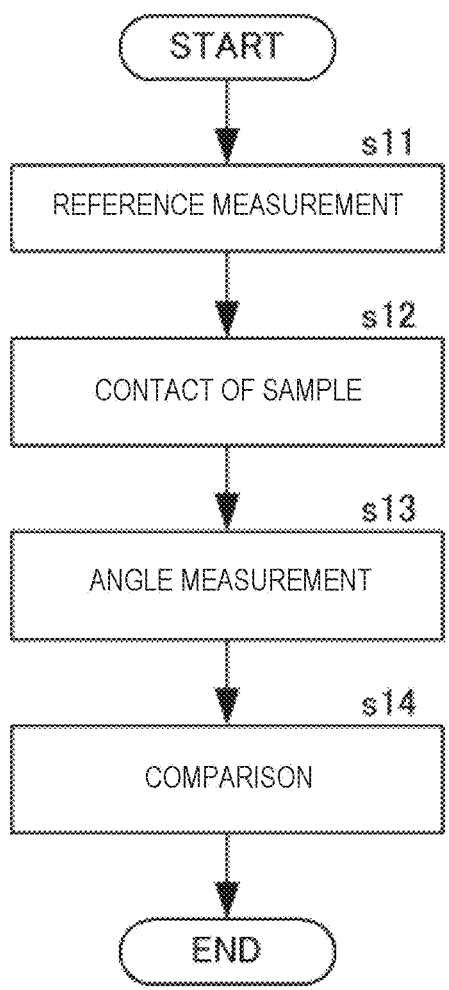
FIG. 9 is a flowchart illustrating a measuring method.

Next, FIG. 9 is a flowchart of a measuring method. The measuring device 15 first may measure a reference peak angle which is a state where the analyte 201 is not coupled to the ligand 102 (s11: corresponding to a first measuring step). For example, the measurement of the reference may be performed in a state where the chip 1 is dry, or in a state where buffer solution is contacted on the upper surface of the chip 1.

As illustrated in FIG. 2, the measuring device 15 is configured so that the chip 1 is installed at a given location, and the light of the light source 10 is introduced into the introductory part 11 from the lower surface of the chip 1. The photodetector 30 may receive the light drawn from the drawn-out part 17, and may be comprised of light-receiving elements which are one-dimensionally or two-dimensionally arranged. The measurement part 31 may acquire intensity information on the light received by each light-receiving element of the photodetector 30, and output them to the controller 32. The controller 32 may record the intensity information on the light of each light-receiving element acquired by the measurement part 31 on a built-in memory (not illustrated) in order to analyze the change in the peak angle of the light received by the photodetector 30.

Then, the sample which contains the analyte 201 to be measured may be contacted with the upper surface of the chip 1 (s12: corresponding to a contacting step). The measuring device 15 may introduce light into the introductory part 11 of the chip 1 while the sample contacting the chip 1, and measure the peak angle of the light drawn from the drawn-out part 17 (s13: corresponding to a second measuring step).

Then, the controller 32 may compare the peak angle information on the reference recorded on the memory with the peak angle information after the sample contacts the chip 1 (s14: corresponding to a detecting step). The controller 32 may presume that the analyte 201 exists if the change in the peak angle is, for example, the given value or more. Alternatively, the controller 32 may estimate the concentration of the analyte 201 based on the amount of change in the peak angle.

Note that, in this embodiment, the reference measurement may be performed before the sample contact. In this case, it may be necessary to correct afterwards the change in the peak angle by a difference between an index of refraction of the medium on the chip 1 during the reference measurement (air or buffer solution) and an index of refraction of the sample. On the other hand, after the sample contact, the peak angle may be measured when the coupling has hardly taken place, so that the measurement is used as the reference. In this case, it may not be necessary to take the index-of-refraction difference of the medium into consideration. However, an error may be caused by small coupling from the sample contact to the reference measurement.

Thus, the measuring device 15 can estimate the existence or the concentration of the analyte 201.

The measurement technique disclosed in this embodiment can adjust the number of reflections and change the sensitivity by changing the length of the chip 1 in the Y-direction. For example, since the chip 1 increases in the number of reflections as the length in the Y-direction may increase, thereby improving the sensitivity.

Moreover, even if the amplitude of the light source 10 changes, the amount of change in the peak angle will not change. Therefore, the stable measurement may be possible, even when the light source is somewhat unstable. Moreover, as described above, the concentration of the analyte 201 can be stably estimated, regardless of the variation in the amount of fixation of the ligand 102, and the variation in the propagating direction of the light in the propagation part 13. Therefore, the measurement technique disclosed in this embodiment can accurately estimate the concentration of the analyte 201 with a simple configuration.

Note that, in FIG. 1, the area where the ligand 102 is fixed is the right angled triangular shape in the plan view, and the length in the Y-direction becomes continuously and linearly lengthened in the X-direction. In this case, since the boundary between the area where the ligand 102 is fixed and the area where the ligand 102 is not fixed becomes one straight line in the plan view, the ligand 102 can be formed, for example, only by masking the upper surface of the propagation layer 101 obliquely with the rubber sheet etc., thereby more easily manufacturing the measurement chip than the reference example. Note that the pattern of the ligand 102 is not limited to the example illustrated in FIG. 1, as long as it is a pattern including the area which changes monotonously in the perpendicular direction perpendicular to the propagating direction of the light.

FIGS. 10(A), 10(B), 10(C) and 10(D), and FIGS. 11(A) and 11(B) are plan views illustrating patterns of the ligand 102 according to modifications.

Figure 10A:
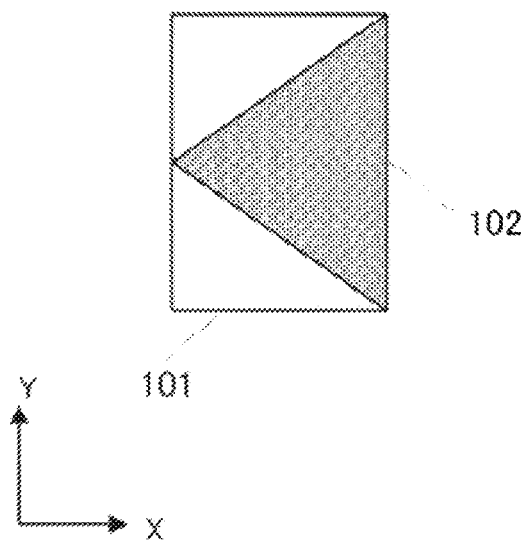
FIGS. 10(A), 10(B), 10(C) and 10(D) are plan views illustrating patterns of a ligand 102 according to a modification.

The area where the ligand 102 is fixed in FIG. 10(A) is an isosceles triangular shape in the plan view, and the length in the propagating direction of the light (Y-direction) is continuously and linearly lengthened in the perpendicular direction (X-direction) perpendicular to the propagating direction of the light. That is, the example of FIG. 10(A) includes the area where the content of the reactant continuously and linearly changes in the perpendicular direction, over the given length in the propagating direction of the light. In this case, since the phase distribution of the light drawn from the drawn-out part 17 is almost the same as that of the example illustrated in FIG. 8, almost the same effect as the example illustrated in FIG. 8 can be expected.

Figure 10B:
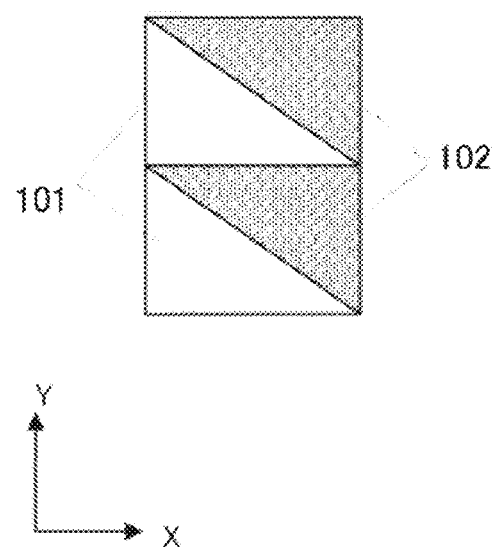

The area where the ligand 102 is fixed in FIG. 10(B) has a shape in which two right angled triangles are lined up in the plan view, and the length in the propagating direction of the light (Y-direction) is continuously and linearly lengthened in the perpendicular direction (X-direction) perpendicular to the propagating direction of the light. That is, the example of FIG. 10(B) includes the area where the content of the reactant changes linearly and continuously in the perpendicular direction, over the given length in the propagating direction of the light. In this case, since the phase distribution of the light drawn from the drawn-out part 17 is almost the same as the example illustrated in FIG. 8, almost the same effect as the example illustrated in FIG. 8 can be expected.

Figure 10C:
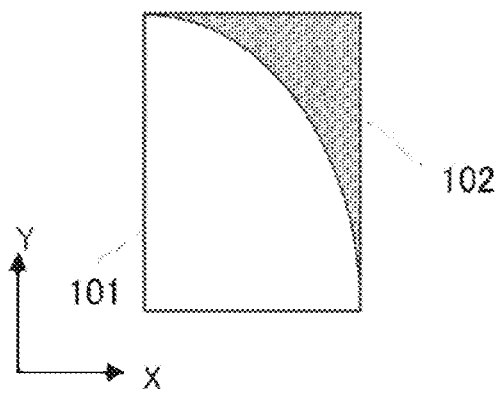

The area where the ligand 102 is fixed in FIG. 10(C) has the length in the propagating direction of the light (Y-direction) being continuously and nonlinearly lengthened in the perpendicular direction (X-direction) perpendicular to the propagating direction of the light. In the example of FIG. 10(C), the content density of the reactant is uniform, and the given length changes continuously in the perpendicular direction (X-direction). In this case, while the moving direction of the light changes, the spreading angle of the light may also change. Therefore, elements other than the moving direction of the light may also change.

Figure 10D:
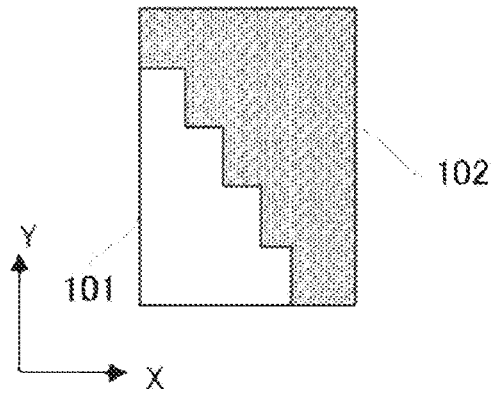

The area where the ligand 102 is fixed in FIG. 10(D) is a stairs-like shape in a plan view, and the length in the propagating direction of the light (Y-direction) changes discontinuously in the perpendicular direction (X-direction) perpendicular to the propagating direction of the light. In this case, diffraction light may appear, and the moving direction of each order of the diffraction light, and the intensity ratio may change.

Figure 11A:
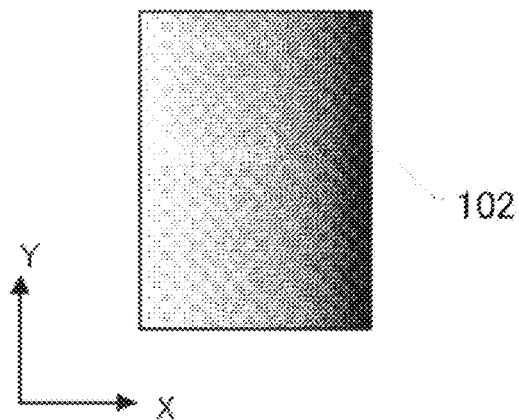
FIGS. 11(A) and 11(B) are plan views illustrating patterns of the ligand 102 according to a modification.

The examples of FIGS. 1, 10(A), 10(B), 10(C) and 10(D) are examples in which the content density of the reactant is uniform, and the given length changes monotonously in the perpendicular direction. The examples of FIGS. 1, 10(A), 10(B) and 10(C) are examples in which the content density of the reactant is uniform, and the given length changes continuously in the perpendicular direction. The example of FIGS. 1, 10(A) and 10(B) are examples in which the content density of the reactant is uniform, and the given length changes linearly in the perpendicular direction. On the other hand, although the area where the ligand 102 is fixed in FIG. 11(A) is the entire surface in the plan view, the density (the content density of the ligand 102 in upper surface of the propagation layer 101) may change linearly in the perpendicular direction (X-direction) perpendicular to the propagating direction of the light. That is, in the example of FIG. 11(A), the given length is constant in the perpendicular direction, and the content density of the reactant changes monotonously in the perpendicular direction. Also in this case, the moving direction of light may change.

Figure 11B:
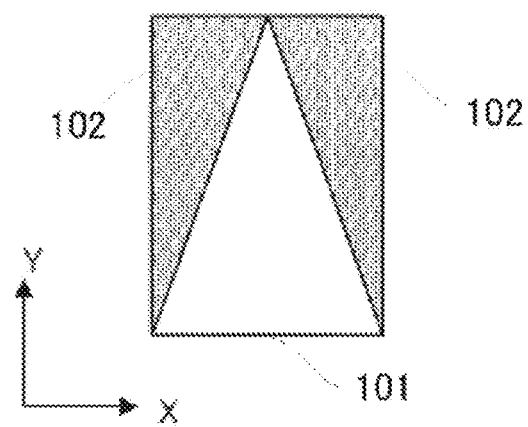

The area where the ligand 102 is fixed in FIG. 11(B) is the exterior of an isosceles triangle in the plan view, and the length in the propagating direction of the light (Y-direction) is continuously and linearly lengthened after continuously and linearly shortened, in the perpendicular direction (X-direction) perpendicular to the propagating direction of the light. In this case, when the phase differences between the center and both ends of the light drawn from the drawn-out part 17 are small, the spreading angle of the light may change according to the phase difference, and when the phase differences are large, the light may be divided into two, and the angle between the respective moving directions may change according to the phase difference. The absolute amount of the phase difference can be estimated based on the difference between the peak angles of the two divided lights, and there may be a merit that the amount of fixation of the ligand 102 and the concentration of the analyte 201 can be estimated without the reference light.

The pattern of this embodiment illustrated in FIGS. 8(A) and 8(B), and the patterns according to the modifications illustrated in FIGS. 10(A), 10(B), 10(C) and 10(D), and FIGS. 11(A) and 11(B) can of course attain similar effects even when the patterns are reversed with respect to the X-axis and the Y-axis, and the area where the ligand 102 is fixed and the area where the ligand 102 is not fixed are reversed, and these reversed patterns are combined with each other.

Figure 12A:
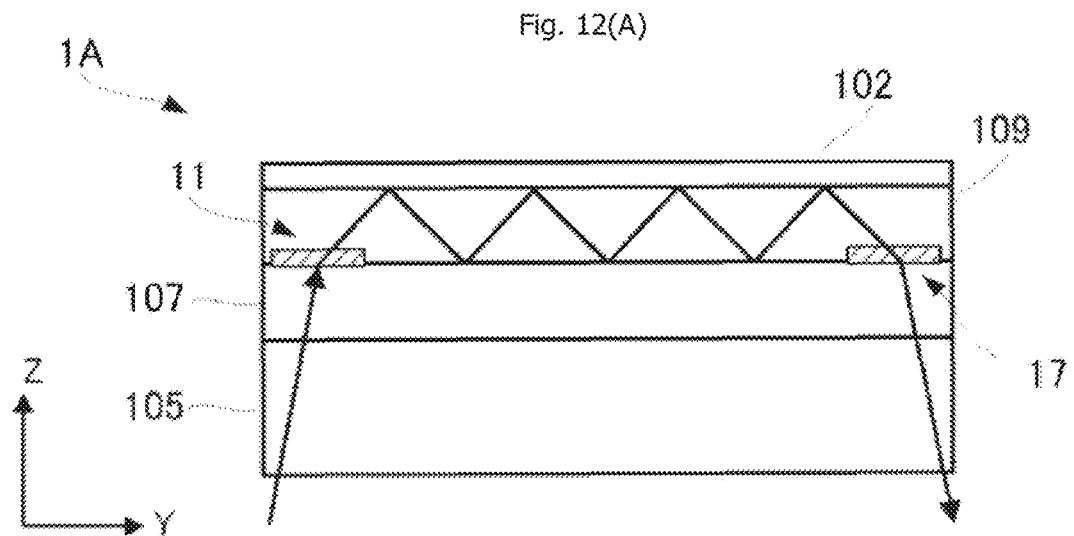
FIG. 12(A) is a cross-sectional view of a chip 1A according to an application example.
Figure 12B:
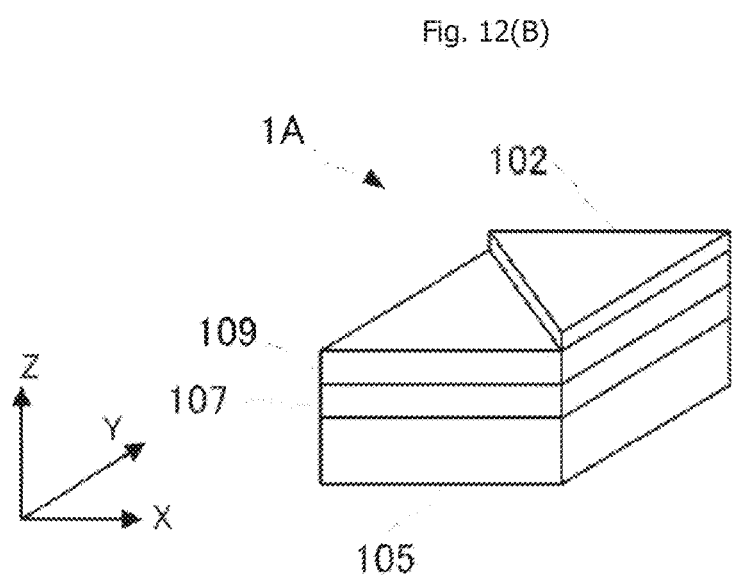
FIG. 12(B) is a perspective view of the chip 1A according to the application example.

Next, FIGS. 12(A) and 12(B) are a cross-sectional view and a perspective view of a chip 1A according to an application example, respectively. In the chip 1A, a propagation layer 109 may be disposed on an upper surface of a base material 105, such as glass, through an intermediate layer 107. Material having an index of refraction about the same as the sample (e.g., fluororesin material of which the index of refraction is about 1.34) may be used for the intermediate layer 107. The ligand 102 may be formed on the upper surface of the propagation layer 109. The pattern of the ligand 102 may be similar to that of the chip 1.

The chip 1A may have the length in the Z-direction of the propagation layer 109 (thickness) shorter (thinner) than the propagation layer 101. Since the shape of the propagation layer 109 is maintained by the base material 105 with the length in the Z-direction of about 0.1 mm, the length in the Z-direction can shortened, for example, to about tens of nm to about hundreds of nm.

Since the propagation layer increases in the number of reflections as the length in the Y-direction becomes longer and the length in the Z-direction becomes shorter, the sensitivity may improve. However, when the length in the Y-direction is lengthened, the amount of the sample to be contacted with the measurement chip may be needed more. Thus, the chip 1A of the application example may be shortened in the length in the Z-direction to tens of nm to hundreds of nm, so that it is configured to be a mode in which a certain amount of sensitivity can be secured, even if the length in the Y-direction is shortened (for example, 1 mm or less).

Figure 13A:
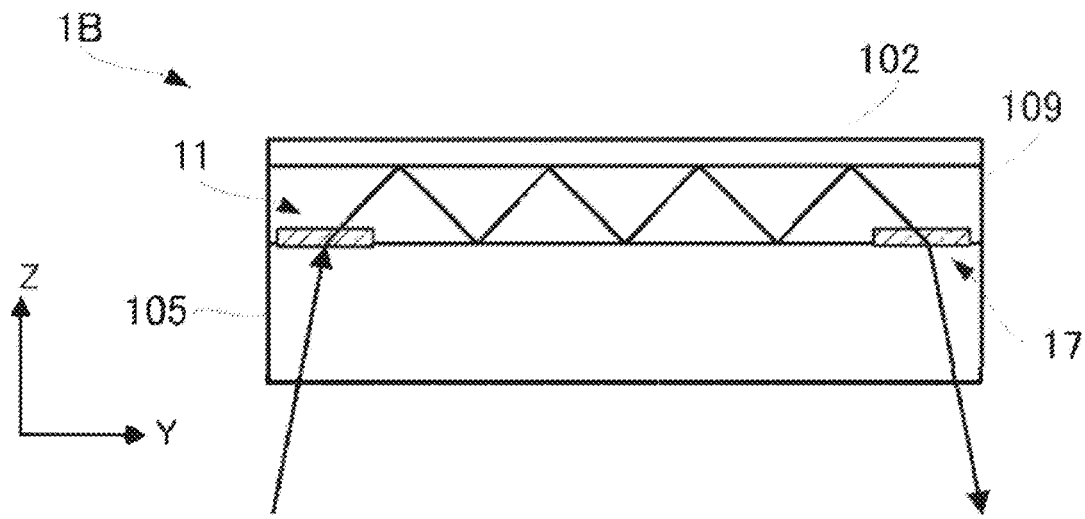
FIG. 13(A) is a cross-sectional view of a chip 1B according to an application example.
Figure 13B:
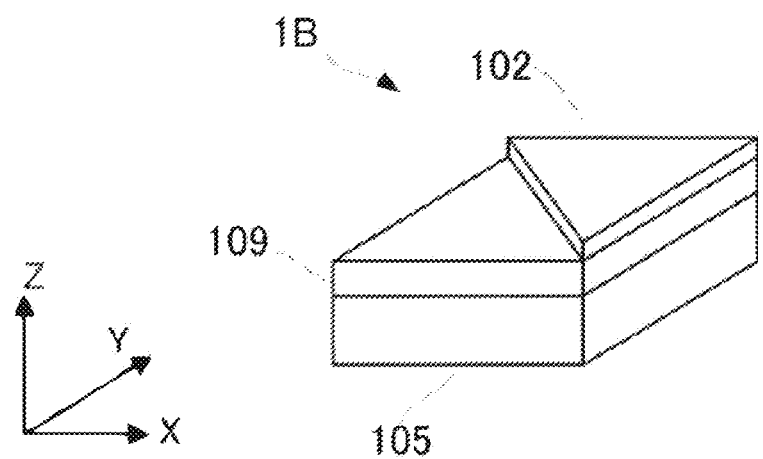
FIG. 13(B) is a perspective view of the chip 1B according to the application example.

Moreover, the intermediate layer 107 may not be essential. For example, as illustrated in FIGS. 13(A) and 13(B), it is also possible to constitute a chip 1B without the intermediate layer 107. Also in this case, it is possible to shorten the length in the Z-direction of the propagation layer 109 to about tens of nm to about hundreds of nm. However, since the length in the Z-direction can be shortened and the propagation angle can be deeper if there is the intermediate layer 107, the number of reflections and the amount of phase shift during reflection can be increased.

Figure 14A:
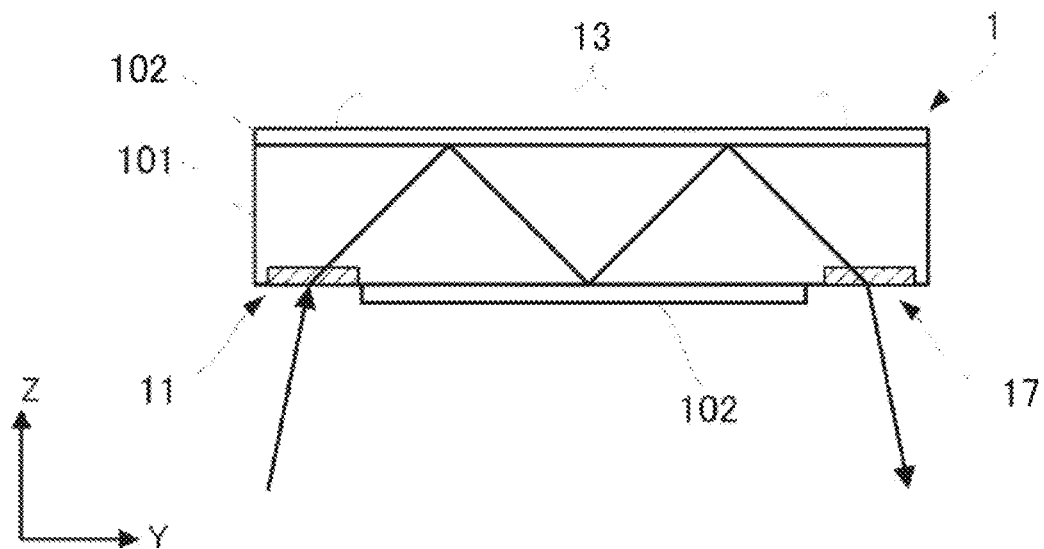
FIG. 14(A) is a cross-sectional view of the chip 1 where the ligand 102 is formed in an upper surface and a lower surface of the chip 1.
Figure 14B:
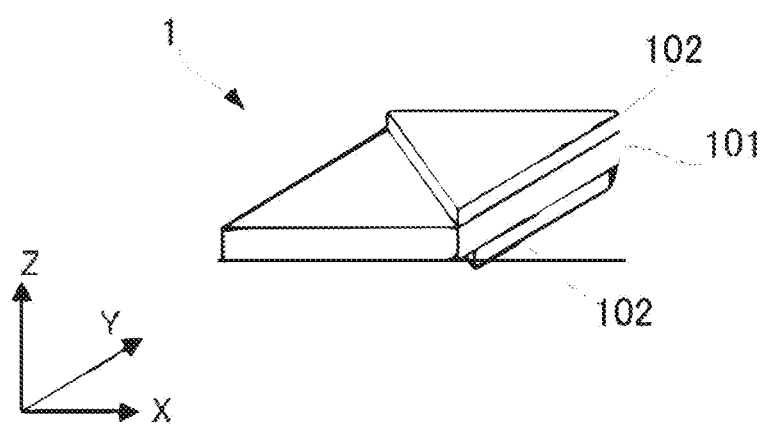
FIG. 14(B) is a perspective view of the chip 1.

Note that although in this embodiment the ligand 102 is formed in the upper surface of the propagation layer 101, it is also possible to constitute a measurement chip, for example, by forming the ligand 102 in the upper surface and the lower surface of the propagation layer 101, as illustrated in FIGS. 14(A) and 14(B).

Moreover, although in this embodiment the concentration of the analyte 201 is estimated, this is applied to the case where the affinity of the analyte 201 and the ligand 102 (a dissociation constant, or an association rate constant and a dissociation rate constant) is known, and the concentration is unknown. On the contrary, when the affinity of the analyte 201 and the ligand 102 is unknown, and the concentration is known, it is also possible to estimate the affinity of the analyte 201 and the ligand 102.

Moreover, although in this embodiment the antigen and the antibody are illustrated as the combination of the analyte 201 and the ligand 102, it may not be limited to this configuration, and the combination may be enzyme and a ground substance, hormone and a receptor, DNA complementary pair, etc. Also in these cases, it may be needless to say that the amount of phase shift during the total reflection differs between the area where the ligand 102 is fixed and the area where the ligand 102 is not fixed, and the amount of phase shift changes according to the coupling of the analyte 201.

Moreover, the technique disclosed in this embodiment may be also applicable to reactions accompanied by the index-of-refraction change, other than the coupling reaction of biomolecules. As one example, the technique disclosed in this embodiment is applicable to a gas sensor etc. In this case, the gas may be the analyte 201 and a chemical substance of which the index of refraction changes by reacting with the gas may be the ligand 102.

TERMINOLOGY

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules executed by a computing system that includes one or more computers or processors. The code modules may be stored in any type of non-transitory computer-readable medium or other computer storage device. Some or all the methods may be embodied in specialized computer hardware.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks and modules described in connection with the embodiments disclosed herein can be implemented or performed by a machine, such as a processor. A processor can be a microprocessor, but in the alternative, the processor can be a controller, microcontroller, or state machine, combinations of the same, or the like. A processor can include electrical circuitry configured to process computer-executable instructions. In another embodiment, a processor includes an application specific integrated circuit (ASIC), a field programmable gate array (FPGA) or other programmable device that performs logic operations without processing computer-executable instructions. A processor can also be implemented as a combination of computing devices, e.g., a combination of a digital signal processor (DSP) and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C. The same holds true for the use of definite articles used to introduce embodiment recitations. In addition, even if a specific number of an introduced embodiment recitation is explicitly recited, those skilled in the art will recognize that such recitation should typically be interpreted to mean at least the recited number (e.g., the bare recitation of "two recitations," without other modifiers, typically means at least two recitations, or two or more recitations).

It will be understood by those within the art that, in general, terms used herein, are generally intended as "open" terms (e.g., the term "including" should be interpreted as "including but not limited to," the term "having" should be interpreted as "having at least," the term "includes" should be interpreted as "includes but is not limited to," etc.).

For expository purposes, the term "horizontal" as used herein is defined as a plane parallel to the plane or surface of the floor of the area in which the system being described is used or the method being described is performed, regardless of its orientation. The term "floor" can be interchanged with the term "ground" or "water surface". The term "vertical" refers to a direction perpendicular to the horizontal as just defined. Terms such as "above," "below," "bottom," "top," "side," "higher," "lower," "upper," "over," and "under," are defined with respect to the horizontal plane.

As used herein, the terms "attached," "connected," "mated," and other such relational terms should be construed, unless otherwise noted, to include removable, moveable, fixed, adjustable, and/or releasable connections or attachments. The connections/attachments can include direct connections and/or connections having intermediate structure between the two components discussed.

Unless otherwise explicitly stated, numbers preceded by a term such as "approximately", "about", and "substantially" as used herein include the recited numbers, and also represent an amount close to the stated amount that still performs a desired function or achieves a desired result. For example, unless otherwise explicitly stated, the terms "approximately", "about", and "substantially" may refer to an amount that is within less than 10% of the stated amount. Features of embodiments disclosed herein preceded by a term such as "approximately", "about", and "substantially" as used herein represent the feature with some variability that still performs a desired function or achieves a desired result for that feature.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. A measuring chip, comprising:
    a propagation layer having top and bottom surfaces that reflect light within the propagation layer so that the light propagates in a light propagation direction and within the propagation layer, the propagation layer including:
        an introductory part embedded in a first end of the bottom surface of the propagation layer and configured to introduce the light into the propagation layer so as to propagate the light in the light propagation direction; and
        a drawn-out part embedded in a second end of the bottom surface of the propagation layer opposite from the first end, and configured to draw the light propagated in the light propagation direction from the propagation layer; and
    a reaction part having a bottom surface directly on the top surface of the propagation layer, the propagation layer having an area larger than an area of the reaction part, the reaction part comprising a reactant that is reactive with a substance to be placed on an upper surface of the reaction part for detection,
    wherein the area of the reaction part has a length in a direction perpendicular to the light propagation direction that increases from the first end to the second end of the propagation layer.

2. The measurement chip of claim 1, wherein the reaction part is formed as a flat region on the top surface of the propagation layer between the introductory part and the drawn-out part.

3. The measurement chip of claim 1, wherein the reaction part includes the area where the length of the reaction part of the light propagation direction continuously increases or decreases along the direction perpendicular to the light propagation direction.

4. The measurement chip of claim 1, wherein the reaction part includes the area where the length of the reaction part of the light propagation direction linearly increases or decreases along the direction perpendicular to the light propagation direction.

5. The measurement chip of claim 1, wherein a content density of the reactant forming the reaction part is uniform.

6. The measurement chip of claim 1, wherein the reaction part includes a first reaction part and a second reaction part respectively formed on opposing surfaces of the propagation layer.

7. The measurement chip of claim 1, wherein a side of the reaction part is located in a common plane as a side of the propagation layer.

8. The measurement chip of claim 1, wherein the reaction part has a shape of a right triangle in a plan view.

9. The measurement chip of claim 1, wherein the reaction part has a shape of an isosceles triangle in a plan view.

10. The measurement chip of claim 1, wherein the reaction part comprises a first and second reaction part placed on the top surface of the propagation layer in the light propagation direction, each having a shape of a right triangle in a plan view, wherein a side of each of the first and second reaction parts are in a common plane as a side of the propagation layer.

11. The measurement chip of claim 1, wherein the reaction part comprises a first and second reaction part placed on the top surface of the propagation layer, each having a shape of a right triangle in a plan view, wherein a side of the first reaction part is in a common plane as a first side of the propagation layer and a side of the second reaction part is in a common plane of a second side of the propagation layer.

12. The measurement chip of claim 1, wherein the length of the reaction part in the direction perpendicular to the light propagation direction increases linearly from the first end to the second end of the propagation layer.

13. The measurement chip of claim 1, wherein the length of the reaction part in the direction perpendicular to the light propagation direction increases exponentially from the first end to the second end of the propagation layer.

14. The measurement chip of claim 1, wherein the length of the reaction part in the direction perpendicular to the light propagation direction increases step-wise from the first end to the second end of the propagation layer.

15. The measurement chip of claim 1, wherein the reaction part is configured to change a phase of the light propagated within the propagation layer and thereby change a moving direction of the light to a direction approaching perpendicular to the light propagation direction.

16. A measuring device in which the measurement chip of claim 1 is disposed, comprising:
- a light source configured to provide the light to the introductory part of the propagation layer;
- a photodetector configured to receive the light drawn from the drawn-out part of the propagation layer; and
- a controller comprising circuitry configured to analyze a pattern of the light received by the photodetector.

* * * * *